United States Patent [19]

Felder et al.

[11] 4,246,164

[45] Jan. 20, 1981

[54] PROCESS FOR THE RESOLUTION OF (+)- AND (−)-6-METHOXY-α-METHYL-2-NAPHTHALENEACETIC ACID

[75] Inventors: Ernst Felder, Riva San Vitale, Switzerland; Davide Pitre, Milan, Italy; Hans Zutter, Schaffhausen, Switzerland

[73] Assignee: Syntex Corporation, Panama

[21] Appl. No.: 55,427

[22] Filed: Jul. 6, 1979

[30] Foreign Application Priority Data

Jul. 19, 1978 [CH] Switzerland ............... 7777/78

[51] Int. Cl.³ .................... C07C 91/10; C07C 65/24; C07B 19/00
[52] U.S. Cl. .................... 260/501.17; 562/466; 562/401; 564/507
[58] Field of Search ............ 260/501.17, 584 R; 562/466, 401

[56] References Cited

U.S. PATENT DOCUMENTS

| | | | |
|---|---|---|---|
| 2,016,962 | 10/1935 | Flint et al. | 260/584 R |
| 2,016,963 | 10/1935 | Flint et al. | 260/584 R |
| 3,904,682 | 9/1975 | Fried et al. | 562/466 |
| 3,904,683 | 9/1975 | Day et al. | 562/466 |
| 3,906,038 | 9/1975 | Fried et al. | 260/501.18 |

OTHER PUBLICATIONS

Greenstein et al., Chem. of the Amino Acids, John Wiley & Sons, Inc., N.Y. vol. 1, pp. 715-728 (1961).

*Primary Examiner*—Joseph E. Evans
*Assistant Examiner*—G. T. Breitenstein
*Attorney, Agent, or Firm*—Joseph I. Hirsch; John A. Dhuey

[57] ABSTRACT

The subject of the invention is a process for resolving mixtures of (+)- and (−)-6-methoxy-α-methyl-2-naphthaleneacetic acid into the enantiomers thereof, characterized in that N-methyl-D-glucamine [=1-deoxy-1-(methylamino)-D-glucitol] is used as the resolving agent, so that the 6-methoxy-α-methyl-2-naphthaleneacetic acid is converted into the corresponding diastereoisomeric N-methyl-D-glucamine salt pair which, because of very different solubilities, can be separated easily and completely with high yield.

19 Claims, No Drawings

PROCESS FOR THE RESOLUTION OF (+)- AND (−)-6-METHOXY-α-METHYL-2-NAPHTHALENEACETIC ACID (+)-6-methoxy-α-methyl-2-naphthaleneacetic acid [=D-2-(6-methoxy-2-naphthyl)propionic acid] is an effective antiphlogistic/analgetic/antipyretic.

According to German Application No. 2,039,602, for example, it is obtained from the racemate by selective biological degradation or by preparation of the diastereoisomer salts of 6-methoxy-α-methyl-2-naphthaleneacetic acid with a resolved, optically active amine base, such as cinchonidine, and then separation of the resulting diastereoisomers by fractional crystallization. The separated diastereoisomer salts are then hydrolyzed with strong acids, yielding the corresponding (+)- or (−)-6-methoxy-α-methyl-2-naphthaleneacetic acids.

The racemate of 6-methoxy-α-methyl-2-naphthaleneacetic acid cannot be resolved by spontaneous separation and preferential selective crystallization of one of the enantiomers.

In addition to cinchonidine, the following compounds, inter alia, are proposed in German Applications Nos. 2,007,177 and 2,008,272 as optically active amine bases for the separation step: the naturally occurring alkaloids, anabasine, brucine, conessine, cinchonicine, cinchonine, D-desoxyephedrine, L-ephedrine, epiquinine, morphine, quinidine, quinine, strychnine, dehydroabietylamine, and solanidine as well as cholesterylamine, D-menthylamine, glucosamine, primary, secondary and tertiary amines such as L-2-amino-1-propanol, L-2-aminobutanol, D-2-aminobutanol, D-threo-2-amino-1-p-nitrophenyl-1,3-propanediol, D-amphetamine, L-2-benzylamino-1-propanol, D-4-dimethylamino-1,2-diphenyl-3-methyl-2-butanol, D-α-(1-naphthyl)ethylamine, L-α-(1-naphthyl)ethylamine, D-α-methylbenzylamine and L-α-methylbenzylamine.

The alkaloids cinchonidine, dehydroabietylamine and quinine are preferred according to German Applications Nos. 1,934,460, 2,013,641, 2,007,177, 2,005,454, 2,008,272 and 2,039,602.

The other alkaloids and bases were mentioned in Example 7 of German Application No. 2,007,177 and in Example 3 of German Application No. 2,008,272.

German Application No. 2,005,454 claims pharmaceutically acceptable salts of 6-methoxy-α-methyl-2-naphthaleneacetic acid which are suitable for treatment and alleviation of inflammations, fevers, etc. Among the salts claimed broadly but not described in more detail are the N-methyl-D-glucamine salts. The N-methyl-D-glucamine salt of (+)6-methoxy-α-methyl-2-naphthaleneacetic acid is mentioned in Example 26 of German Application No. 2,005,454 as a possible end product. This salt was prepared by the reaction of (+)-6-methoxy-α-methyl-2-naphthaleneacetic acid with N-methyl-D-glucamine. The N-methyl-D-glucamine salts of the racemic mixture of 6-methoxy-α-methyl-2-naphthaleneacetic acid, however, have not been before described.

Asymmetric bases with a carbohydrate structure are generally unknown as resolving agents (cf. N. L. Allinger and E. L. Eliel, Topics in Stereochemistry, Vol. 6, Wiley-Interscience, New York, 1971, Chapter: Resolving Agents and Resolution in Organic Chemistry by S. H. Wilen; and S. H. Wilen, Tables of Resolving Agents and Optical Resolutions, Edited by E. L. Eliel, 1972, University of Notre Dame Press) and, prior to this invention, have been considered to be unsuitable for that purpose.

German Application No. 2,007,177 had proposed glucosamine for resolution of 6-methoxy-α-methyl-naphthaleneacetic acid. Nowhere does it contain a specific example, however.

Glucosamine [=2-amino-2-deoxy-D-glucose] is very difficult to synthesize, can be obtained practically only from chitin, and is relatively unstable. The solubility of its salts with (+)- and (−)-A (where A is 6-methoxy-α-methyl-2-naphthaleneacetic acid) was determined to elucidate the suitability of this material as a resolving agent (Table 1).

TABLE 1

| | Solubility of the glucosamine salts | | | |
|---|---|---|---|---|
| Solvent | Salt of (+) A with D-glucosamine $[\alpha]_D^{20} = 38.95°$ mp = 60–63° C. decomp. 20° C. boiling temp. | | Salt of (−) A with D-glucosamine $[\alpha]_D^{20} = 37.41°$ mp = 90–100° C. decomp. 20° C. boiling temp. | |
| $H_2O$ | insol. | decomp. | 1 | decomp. |
| $CH_3OH$ | 50 | decomp. | 3.3 | decomp. |
| $C_2H_5OH$, 95% | 2.5 | decomp. | 1 | decomp. |
| $C_2H_5OH$ absolute | <1 | decomp. | <1 | decomp. |

Table 1 shows that the undesired isomer, i.e. the (−)A form, could perhaps be isolated using the glucosamine salt. Even at temperatures as low as 40° C., which are unavoidable in practice, the glucosamine salts are unstable as they decompose. This decisively impairs their preparation, isolation and perhaps regeneration. In fact, from a commercial viewpoint, glucosamine is unsuitable as a resolving agent for mixtures of (+)- and (−)-6-methoxy-α-methyl-2-naphthaleneacetic acid, which supports the opinion that assymetric bases with a carbohydrate structure are very poor resolving agents.

Surprisingly, it has now been found that N-methyl-D-glucamine is commercially suitable for resolution of mixtures of (+)- and (−)-6-methoxy-α-methyl-2-naphthaleneacetic acid into the enantiomers thereof.

The subject of the invention is, therefore, a process for resolving mixtures of (+)- and (−)-6-methoxy-α-methyl-2-naphthaleneacetic acid, or a soluble salt thereof, into the enantiomers thereof, characterized in that N-methyl-D-glucamine [=1-deoxy-1-(methylamino)-D-glucitol], or a salt thereof, is used as the resolving agent.

For this purpose, a mixture of (+)- and (−)-6-methoxy-α-methyl-2-naphthaleneacetic acid is combined with N-methyl-D-glucamine and the resulting pair of (+)- and (−)-6-methoxy-α-methyl-2-naphthaleneacetic acid N-methyl-D-glucamine salts are subjected to fractional crystallization.

Alternatively, soluble salts of (+)- and (−)-6-methoxy-α-methyl-2-naphthaleneacetic acid can be resolved with appropriate salts of N-methyl-D-glucamine.

The (+)- and (−)-6-methoxy-α-methyl-2-naphthaleneacetic acid N-methyl-D-glucamine salts obtained are decomposed individually by acid cleavage, for example with a mineral acid, with the acids precipitating, or by base cleavage followed by acidification to form the free acids. The desired (+)-form can be obtained in pure form. Then using known methods, the (−)-form is racemized and N-methyl-D-glucamine is recovered from the acidic mother liquors.

It has been found that the salts of the optically active base N-methyl-D-glucamine [=1-deoxy-1-(methylamino)-D-glucitol] with (+)- and (−)-6-methoxy-α-methyl-2-naphthaleneacetic acid have extremely large solubility differences, which are ideal for separation of the diastereoisomers. The salt of the desired (+)-6-methoxy-α-methyl-2-naphthaleneacetic acid with N-methyl-D-glucamine is much more poorly soluble than is the corresponding salt of (−)-6-methoxy-α-methyl-2-naphthaleneacetic acid and so can be very easily obtained in pure form. The solubilities of the diastereoisomeric salt pairs of (+)- and (−)-6-methoxy-α-methyl-2-naphthaleneacetic acid with N-methyl-D-glucamine in various solvents are listed in Table 2 where A is as defined above.

TABLE 2

| Solvent | Salt of (+)A with N-methyl-D-glucamine 20° C. | boiling temp. | Salt of (−)A with N-methyl-D-glucamine 20° C. | boiling temp. |
|---|---|---|---|---|
| $H_2O$ | 25 | 100 | 70 | 100 |
| $CH_3OH$ | 1.3 | 6.5 | 18 | 100 |
| $(CH_3)_2CHOH$ | 0.02 | 0.16[1] | 0.16 | 1.7[1] |

[1] at reflux

The solubility differences are very pronounced even in water, which was not the case for any of the other pairs studied.

The solubility differences in cold and hot methanol are considerably greater. They are 1.3:18 (1:14) at room temperature and 6.5:100 (1:15.4) at boiling temperature, and favor isolation of the desired isomer of the (+)A form. This favorable condition and the higher absolute value of the solubility of the salt of (−)A with N-methyl-D-glucamine permit economic separation with a minimum of solvent consumption and a maximum of resolving effect, i.e. with highest optical purity of the desired product and simultaneously with high yield.

The use of N-methyl-D-glucamine for resolution of 6-methoxy-α-methyl-2-naphthaleneacetic acid is advantageous for the additional reason that N-methyl-D-glucamine is very readily accessible via reduction of D-glucose (grape sugar), which is inexpensive and available in unlimited quantities, in the presence of methylamine.

The resolution contemplated by this invention is conducted in an inert organic solvent having a pronounced difference between the solubilities of the salt of (+)-6-methoxy-α-methyl-2-naphthaleneacetic acid with N-methyl-D-glucamine and the salt of (−)-6-methoxy-α-methyl-2-naphthaleneacetic acid with N-methyl-D-glucamine, generally at temperatures between room or ambient temperature and an elevated temperature generally up to the reflux temperature of the solvent utilized. The salt of (+)-6-methoxy-α-methyl-2-naphthaleneacetic acid with N-methyl-D-glucamine should be significantly less soluble in the solvent than is the salt of (−)-6-methoxy-α-methyl-2-naphthaleneacetic acid with N-methyl-D-glucamine and, accordingly, upon the cooling of a heated solution thereof, generally to or about ambient or room temperature, such salt of (+)-6-methoxy-α-methyl-2-naphthaleneacetic acid with N-methyl-D-glucamine will be preferentially crystallized therefrom. Suitable solvents include $C_1$ to $C_{10}$ monohydric alcohols, such as, for example, methanol, ethanol, n-propanol, isopropanol, butanol, pentanol, hexanol, cyclohexanol, 2-ethylhexanol, benzyl alcohol, furfuryl alcohol, and the like, $C_2$ to $C_6$ dihydric alcohols, such as, for example, ethylene glycol, 1,2-propylene glycol, 1,3-propylene glycol, and the like, $C_3$ to $C_4$ trihydric alcohols, such as for example, glycerol, and the like, $C_3$ to $C_{11}$ ketones, such as, for example, acetone, acetylacetone, ethyl methyl ketone, diethyl ketone, di-n-propyl ketone, diisopropyl ketone, diisobutyl ketone, and the like. Other solvents include mono- and di(lower)alkyl ether of ethylene glycol and diethylene glycol, dimethylsulfoxide, sulfolanes, formamide, dimethylformamide, N-methyl pyrrolidone, pyridine, dioxane, dimethylacetamide, and the like. The $C_1$ to $C_3$ alcohols, e.g. methanol and isopropanol, particularly methanol, are the presently preferred solvents. Sufficient water can be added to the solvent if needed to solubilize all of the materials which have been added thereto.

The starting material [i.e., the mixture of (+)-6-methoxy-α-methyl-2-naphthaleneacetic acid and (−)-6-methoxy-α-methyl-2-naphthaleneacetic acid] is heated to an elevated temperature, generally to a temperature in the range of from about 60° C. to about 100° C. or the reflux temperature of the solvent, in the presence of the N-methyl-D-glucamine to solubilize all of the materials which have been added to the solvent. If desired, the solvent can be held at the elevated temperature until all of the materials have gone into solution. After the solution has been held at the elevated temperature for the desired length of time, it is slowly cooled to ambient temperature. During the cooling process, the solution is preferably seeded with a salt of (+)-6-methoxy-α-methyl-2-naphthaleneacetic acid with N-methyl-D-glucamine. The crystalline precipitate which results is enriched in the salt of (+)-6-methoxy-α-methyl-2-naphthaleneacetic acid with N-methyl-D-glucamine. The final temperature to which the solution is taken is chosen by practical considerations but generally is selected so that the temperature difference will be sufficient to provide a high yield of crystals. The crystallizing mixture can be maintained at the lower temperature until crystallization is complete, or nearly so, usually for about 30 minutes to about several hours or so. The crystalline precipitate which results is removed by filtration and washed.

The crystalline material which is obtained at this step in the process [i.e., a material which is enriched in the salt of (+)-6-methoxy-α-methyl-2-naphthaleneacetic acid with N-methyl-D-glucamine], after separation by filtration and washing, can be charged to water and heated, if necessary, to redissolve the crystalline material. The resulting solution is acidified for example with a mineral acid, such as sulphuric acid or hydrochloric acid, or an organic acid such as acetic acid or p-toluenesulfonic acid and the crystalline precipitate so obtained is separated by filtration, washed and dried. There results a white crystalline product substantially enriched in (+)-6-methoxy-α-methyl-2-naphthaleneacetic acid. Alternatively, the material enriched in the salt of (+)-6-methoxy-α-methyl-2-naphthaleneacetic acid with N-methyl-D-glucamine can be treated with a strong base, such as for example, potassium hydroxide or another strong base having a pKa value greater than 10, to cleave the salt, followed by acidification with, for example, a mineral acid such as hydrochloric acid or sulfuric acid or an organic acid such as acetic acid, to give, after filtration, washing and drying, a white crystalline product substantially enriched in (+)-6-methoxy-α-methyl-2-naphthaleneacetic acid.

Prior to redissolving of the material enriched in the salt of (+)-6-methoxy-α-methyl-2-naphthaleneacetic acid with N-methyl-D-glucamine and subsequent acidification to obtain (+)-6-methoxy-α-methyl-2-naphthaleneacetic acid, it is generally desirable to redissolve the enriched salt material in further solvent material, heating the solvent to the desired temperature, followed by seeding of the resultant solution with the salt of (+)-6-methoxy-α-methyl-2-naphthaleneacetic acid with N-methyl-D-glucamine, and cooling to effect one or more further recrystallizations. Each such recrystallizations further increases the proportion of the salt of (+)-6-methoxy-α-methyl-2-naphthaleneacetic acid with N-methyl-D-glucamine in the recrystallized material. Product having a purity on the order of about 97–99% (+)-6-methoxy-α-methyl-2-naphthaleneacetic acid can be obtained with merely one recrystallization step prior to the redissolution of the resultant crystalline product and subsequent acidification.

The material enriched in (−)-6-methoxy-α-methyl-2-naphthaleneacetic acid or the N-methyl-D-glucamine salt thereof can be processed to recover (−)-6-methoxy-α-methyl-2-naphthaleneacetic acid which can then be racemized according to known techniques to give a material having a higher content of (+)-6-methoxy-α-methyl-2-naphthaleneacetic acid. See, for example, Dyson U.S. Pat. No. 3,686,183. This material can be recycled, either alone or in combination with other mixtures of (+)- and (−)-6-methoxy-α-methyl-2-naphthaleneacetic acid, to provide additional starting material for the resolution process of this invention.

The amount of N-methyl-D-glucamine employed [on a molar basis relative to the (+)- and (−)-6-methoxy-α-methyl-2-naphthaleneacetic acid being resolved] in accordance with the present invention ranges from between about 50% and 100%. However, as only about 50% [on a molar basis relative to the (+)- and (−)-6-methoxy-α-methyl-2-naphthaleneacetic acid being resolved] of the N-methyl-D-glucamine is needed to form the more insoluble salt thereof with the (+)-6-methoxy-α-methyl-2-naphthaleneacetic acid, the remainder of the N-methyl-D-glucamine (generally on the order of up to about 40–50 molar %) can be replaced, if desired, with a more inexpensive base, including, for example, an inorganic base such as an alkali metal hydroxide, such as sodium hydroxide or potassium hydroxide, or an organic tertiary amine such as triethylamine, triethanolamine, tri-n-butylamine, etc.

The aqueous mother liquors resulting from the isolation of (+)-6-methoxy-α-methyl-2-naphthaleneacetic acid and (−)-6-methoxy-α-methyl-2-naphthaleneacetic acid contain, for example, salts of the N-methyl-D-glucamine with the acid utilized in the acidification step. Such mother liquors can be treated with an inorganic base to form an insoluble inorganic salt, leaving the N-methyl-D-glucamine in solution, such as, for example, treatment with a suspension of calcium hydroxide to precipitate the corresponding calcium salt, which is removed by filtration. The filtrate is concentrated under vacuum at elevated temperatures to dryness, first removing any further salt, e.g. the calcium salt, which is formed during the early stages of the concentration process. The residue is dissolved in a suitable solvent at an elevated temperature up to the reflux temperature of the solvent, and then cooled to room temperature, to thereby afford the resolving agent as a crystalline precipitate which can be reused, either alone or in combination with new material, in the resolution process of this invention. Alternatively, the N-methyl-D-glucamine can be recovered through use of an anion exchange resin and recycled for reuse.

The terms "mixture of (+)-6-methoxy-α-methyl-2-naphthaleneacetic acid and (−)-6-methoxy-α-methyl-2-naphthaleneacetic acid" is also intended to include those salts thereof which are soluble in the solvent utilized in the resolution process of this invention. Such salts include, for example, the corresponding sodium salts, potassium salts, lithium salts, and the like. Such salts can be prepared by the addition of base, such as an alkali metal hydroxide, for example, sodium or potassium hydroxide, to a solution of the mixture of the (+)- and (−)-6-methoxy-α-methyl-2-naphthaleneacetic acid. The resulting mixture of (+)- and (−)-6-methoxy-α-methyl-2-naphthaleneacetic acid salts can be resolved according to the present invention by use of a salt of the resolving agent which will react to form a salt of (+)-6-methoxy-α-methyl-2-naphthaleneacetic acid with the N-methyl-D-glucamine. Suitable N-methyl-D-glucamine salts include, for example, the hydrochloride salt and the acetate salt. Other salts include the propionate salt, butyrate salt, isobutyrate salt, sulfate salt, nitrate salt, and the like. Accordingly, "N-methyl-D-glucamine" is intended to include those salts thereof which, when used with an appropriate salt of the mixture of (+)- and (−)-6-methoxy-α-methyl-2-naphthaleneacetic acid, will afford the resolution contemplated hereby.

EXAMPLES

EXAMPLE 1

(+)-6-methoxy-α-methyl-2-naphthaleneacetic N-methyl-D-glucamine salt 460.7 g. of racemic 6-methoxy-α-methyl-2-naphthaleneacetic acid (2 mol) and 390.5 g of N-methyl-D-glucamine [=1-deoxy-1-(methylamino)-D-glucitol] (2 mol) were dissolved in 4 liters of boiling methanol.

The solution was filtered to clearness and carefully cooled to 45° C. with slow stirring. 1 G. of (+)-6-methoxy-α-methyl-2-naphthaleneacetic acid N-methyl-D-glucamine salt crystals (obtained in a preliminary test by cooling and rubbing with a glass rod, filtering under suction and washing with some methanol) was now added. Massive crystallization of (+)-6-methoxy-α-methyl-2-naphthaleneacetic acid N-methyl-D-glucamine salt occurred immediately after seeding. The temperature was held at 45° C. and then lowered slowly to 15° C.

The precipitated crystals were filtered off and washed with a little methanol.

Yield: 360 g. of (+)-6-methoxy-α-methyl-2-naphthaleneacetic acid N-methyl-D-glucamine salt, i.e. 84% of theoretical.

Melting point: 156°–158° C.

Specific rotation at 20° C.; conc.=1% in water

| Wavelength λ | 589 | 546 | 436 | 365 |
|---|---|---|---|---|
| $[\alpha]_\lambda^{20}$ ° | −18.59 | −22.85 | −42.53 | −80.63 |

The product obtained (360 g.) was redissolved in 4.4 liters of boiling methanol, filtered, cooled slowly, seeded with authentic material, allowed to crystallize out, cooled, filtered and washed.

Yield: 278 g. of pure (+)-6-methoxy-α-methyl-2-naphthaleneacetic acid N-methyl-D-glucamine salt, i.e. 65% of theoretical.

Melting point: 160°–161° C.
Specific rotation at 20° C.; conc.=1% in water

| Wavelength λ | 589 | 546 | 436 | 365 |
|---|---|---|---|---|
| $[\alpha]_\lambda^{20}$ ° | −20 | −23.95 | −44.83 | −87.19 |

Microanalysis: $C_{21}H_{31}NO_8$:
calc. C 59.28%; N 3.29%
found C 59.58%; N 3.42%.

The mother liquors were completely evaporated to recover the methanol.

The residue from evaporation was dissolved in water and dilute hydrochloric acid was added to acidify the salt solution. The (−)-6-methoxy-α-methyl-2-naphthaleneacetic acid was precipitated.

Amount: 228 g. of (−)-6-methoxy-α-methyl-2-naphthaleneacetic acid, i.e. 99.1% of theoretical.

Melting point: 145°–146° C.
$[\alpha]_D^{20}= -45.8°$ (conc.=1% in chloroform).
(589)Optical purity: 67%.

The product can be converted by racemization back to the racemate, i.e. the starting material, and then re-used in further batches during the resolution process.

EXAMPLE 2

Reuse of the mother liquors

The methanolic mother liquor can be used directly prior to regeneration, in further resolving operations.

A resolving operation as described in Example 1 was carried out with the same quantities of starting materials. Instead of fresh methanol, however, the methanolic mother liquor from a previous equal batch was used.

The first product obtained was:

431 g. of (+)-6-methoxy-α-methyl-2-naphthaleneacetic acid N-methyl-D-glucamine salt, i.e. 100% of theoretical.

Melting point: 155°–158° C.
Specific rotation at 20° C.; conc.=1% in water

| Wavelength λ | 589 | 546 | 436 | 365 |
|---|---|---|---|---|
| $[\alpha]_\lambda^{20}$ ° | −18.52 | −21.41 | −40.5 | −76.6 |

After recrystallization from 4.4 liters of fresh methanol, the product was:

326 g. of (+)-6-methoxy-α-methyl-2-naphthaleneacetic acid N-methyl-D-glucamine salt, i.e. 76% of theoretical.

Melting point: 159°–160° C.
Specific rotation at 20° C.; conc.=1% in water

| Wavelength λ | 589 | 546 | 436 | 365 |
|---|---|---|---|---|
| $[\alpha]_\lambda^{20}$ ° | −20.02 | −24.12 | −45.88 | −88.41 |

The resolution of racemic 6-methoxy-α-methyl-2-naphthaleneacetic acid was continued another 3 times, always using the mother liquor from the preceding operation.

The following material balance was obtained:

Used: 2,303.5 g. of racemic 6-methoxy-α-methyl-2-naphthaleneacetic acid.

Obtained:
1,613.5 g. of (+)-6-methoxy-α-methyl-2-naphthaleneacetic acid N-methyl-D-glucamine salt, i.e. 75.8% of theoretical, 1,120 g. of (−)-6-methoxy-α-methyl-2-naphthaleneacetic acid, $[\alpha]_D^{20}= -47\pm2°$, optical purity 69%.

EXAMPLE 3

(+)-6-methoxy-α-methyl-2-naphthaleneacetic acid 460.7 G. of racemic 6-methoxy-α-methyl-2-naphthaleneacetic acid (2 mol) and 390 g. of N-methyl-D-glucamine are dissolved in 4 liters of boiling methanol. The obtained diastereoisomer pairs are separated by the method described in Example 1.

Obtained: 370 g. of (+)-6-methoxy-α-methyl-2-naphthaleneacetic acid N-methyl-D-glucamine salt, i.e., 86.9% of theoretical.

Melting point: 158°–159° C.
$[\alpha]_D^{20}= -19.1°$, $[\alpha]_{365}^{20}= -83.7°$ (c=1% in water).

The methanolic mother liquors are used to recover the (−)-6-methoxy-α-methyl-2-naphthaleneacetic acid and the N-methyl-D-glucamine.

The obtained salt (370 g) is dissolved in 1750 ml. of water, and the solution is warmed to 80° C. and filtered clear. The solution is acidified by slow addition of 250 ml. of 4 N sulfuric acid at 80° C. with stirring. The suspension obtained is cooled down to 20° C., the product is filtered off and washed with water. The mother liquor is collected. The filtered product is washed with acidified water (0.001 N hydrochloric acid) until the sulfate ions varnish.

Obtained: 196.3 g. of (+)-6-methoxy-α-methyl-2-naphthaleneacetic acid, i.e., 98% of theoretical relative to utilized salt and 85.16% of theoretical relative to utilized racemate.

Melting point: 156°–157° C.; $[\alpha]_D^{20}= +65.2°$.
Content: 99.4%
By-products=negligible
(DC)
Dry loss: 0.1%.

The quality of the product obtained directly in this manner (naproxen) already meets the optical rotation requirements of the health authorities, e.g., as published in the British Pharmacopeia (Addendum 75), wherein $[\alpha]_D^{20}$ of +63° to +68.5° is required.

EXAMPLE 4

Recovery of (−)-6-methoxy-α-methyl-2-naphthaleneacetic acid (A) and recovery of N-methyl-D-glucamine (B) Recovery of (A)

The methanolic mother liquors from the isomeric separation according to Example 3 are evaporated to dryness. The residue is dissolved in 2300 ml. of water at 80° C. By acidifying with 290 ml. of 4 N sulfuric acid, cooling, filtering and drying, analogously to the method described in detail in Example 3, there is obtained: 255 g. of (−)-6-methoxy-α-methyl-2-naphthaleneacetic acid, which can then be racemized, according to known techniques, for recycling.

$$\text{Mat. Bal.} = \frac{\text{yield of (+)- and (−)-6-methoxy-α-methyl-2-napthalene acetic acid}}{\text{starting material (racemate)}} = 98\%$$

Recovery of (B)

The aqueous mother liquors from the isolation of the (+)- and (−)-forms of 6-methoxy-α-methyl-2-naphthaleneacetic acid from Example 3, containing N-methyl-D-glucamine sulfate, are combined, and there is slowly added to it a suspension of calcium hydroxide [obtained by slaking 63.7 g of calcium oxide (i.e., 105% of theoretical, relative to the utilized sulfuric acid) with 250 ml. of water]. Calcium sulfate is formed, most of which precipitates and is filtered off and washed with water. The filtrate is concentrated to a small volume, the newly precipitated calcium sulfate is filtered off and washed with a little water. The filtrate is now concentrated by evaporation at 85°–95° C. in vacuum to dryness.

The evaporation residue is dissolved in 2400 ml. of 95% ethanol with reflux boiling, filtered clear in the hot state, and cooled to 15° C. N-methyl-D-glucamine crystallizes out.

Amount: 351 g. of N-methyl-D-glucamine
Yield: 90% of theoretical
Content: 99%
Melting point: 127°–128° C.
$[\alpha]_D^{20} = -16.95°$.

EXAMPLE 5

Recovery of N-methyl-D-glucamine with the aid of anion exchange resin

For the decomposition of the (+)- and (−)-6-methoxy-α-methyl-2-naphthaleneacetic acid N-methyl-D-glucamine salts and precipitation of the (+)- and (−)-6-methoxy-α-methyl-2-naphthaleneacetic acids, respectively, it is also possible to use hydrochloric acid instead of the sulfuric acid used in Examples 3 and 4(A). Then, N-methyl-D-glucamine hydrochloride remains dissolved in the aqueous phase, from which the chloride ions can be removed more easily by means of ion exchanges than would be possible with sulfate ions.

From a 2 mol starting preparation, the mother liquors thereby obtained from the precipitation of (+)- and (−)-6-methoxyα-methyl-2-naphthaleneacetic acid, which contain N-methyl-D-glucamine hydrochloride, are neutralized with ammonia to pH 7 and then percolated through an ion exchanger column coated with 1.6 liters of Amberlite® IR-120. The exchange resin is then washed with 3.2 liters of deionized water. The chloride ion-containing effluent is discarded.

The N-methyl-D-glucamine is dissolved out of the exchange resin by percolation with 2400 ml. of aqueous ammonia (2.5 N) and 3.2 liters of deionized water. The effluents are combined and concentrated by evaporation to dryness. As described in Example 4, the evaporation residue is recrystallized from 2400 ml. of 95% ethanol.

Amount: 351 g. of N-methyl-D-glucamine
Yield: 90%
Content: 99.1%
Melting point: 127°–128° C.
$[\alpha]_D^{20} = -17°°$.

EXAMPLE 6

4.60 G. of d,l 2-(6-methoxy-2-naphthyl)propionic acid is heated with 1.01 g. of triethylamine (0.5 equivalent) in 20 ml. of 6% toluene in methanol to the reflux temperature of the solvent to dissolve the d,l 2-(6-methoxy-2-naphthyl)propionic acid. 1.95 G. of N-methyl-D-glucamine (0.5 equivalent) are added and the solution is cooled to room temperature (i.e. about 20°–23° C.) to give 3.52 g. of a material enriched in the salt of d 2-(6-methoxy-2-naphthyl)propionic acid with N-methyl-D-glucamine. The latter is dissolved in about 25 ml. of water, treated with hydrochloric acid until acidic at which time a material enriched in d 2-(6-methoxy-2-naphthyl)propionic acid precipitates out of solution and is recovered by filtration ($[\alpha]_D + 48.8°$).

1.00 G. of the material enriched in the salt of d 2-(6-methoxy-2-naphthyl)propionic acid with N-methyl-D-glucamine is recrystallized from 10 ml. of methanol and 20 ml. of ethanol, concentrated at reflux to remove 5 ml. of solvent, and cooled to give 0.85 g. of a recrystallized salt. This material is treated with hydrochloric acid as set forth in the preceding paragraph to give substantially pure d 2-(6-methoxy-2-naphthyl)propionic acid ($[\alpha]_D + 64.6°$).

EXAMPLE 7

50 G. of d,l 2-(6-methoxy-2-naphthyl)propionic acid is slurried with 432 ml. of methanol and 21.1 ml. of toluene and then 42.36 g. of N-methyl-D-glucamine is added to the slurry. The mixture is heated to reflux and the solution becomes clear. The solution is then cooled to 50° C. and seeded with the N-methyl-D-glucamine salt of d 2-(6-methoxy-2-naphthyl)propionic acid. Crystallization begins to occur as the solution is cooled to 45° C.

The temperature is lowered by 10° C. per hour over 3 hours and the solution held at 15° C. for 30 minutes. The solution is filtered, and the resultant cake is washed with 21 ml. of fresh methanol to yield 84.20 g. of wet cake.

The wet cake is then charged directly to 451 ml. of methanol and 21.3 ml. of toluene and heated to reflux with agitation, cooled to 50° C., seeded with the N-methyl-D-glucamine salt of d 2-(6-methoxy-2-naphthyl)propionic acid, further cooled to 15° C. over 2 hours, then held at 15° C. for 30 minutes. The solution is filtered and the wet cake is washed with 50 ml. of 5% toluene in methanol and partly dried to yield 38.77 g. of partially dried cake.

The partially dried cake is charged to 184 ml. of water and heated to 80° C. with agitation. The solution is treated with 0.97 g. of decolorizing carbon for 20 minutes. The solution is then filtered through Celite filter aid and the temperature of the solution raised to 85° C.

51 Ml. of 3.3 N sulphuric acid is added over 30 minutes to yield a precipitate substantially enriched in d 2-(6-methoxy-2-naphthyl)propionic acid. The solution is held at 85° C. for 30 minutes, then cooled to 15° C. over 2 hours. The solution is aged at 15° C. for 30 minutes, filtered, washed to neutrality and dried. 18.84 G. (direct yield=37.68%) of d 2-(6-methoxy-2-naphthyl)propionic acid are obtained ($[\alpha]_D + 64.6°$).

EXAMPLE 8

The procedure of Example 7 is repeated to obtain 20.02 g. (direct yield=40.0%) of d 2-(6-methoxy-2-naphthyl)propionic acid ($[\alpha]_D + 65.4°$).

What is claimed is:

1. Process for resolving mixtures of (+)- and (−)-6-methoxy-α-methyl-2-naphthaleneacetic acid or salts thereof into the enantiomers thereof characterized in that N-methyl-D-glucamine [=1-deoxy-1-(methylamino)-D-glucitol] or a salt thereof is used as the resolving agent.

2. The process according to claim 1, wherein a mixture of (+)- and (−)-6-methoxy-α-methyl-2-naphthaleneacetic acid is combined with N-methyl-D-glucamine and the resulting pair of (+)- and (−)-6-methoxy- α-methyl-2-naphthaleneacetic acid N-methyl-D-glucamine salts are separated by fractional crystallization.

3. Process according to claim 2, characterized in that the salt formation and the separation of the diastereoisomers is performed by fractional crystallization in methanol.

4. Process according to claim 2, characterized in that the (+)- and (−)-6-methoxy-α-methyl-2-naphthaleneacetic acid N-methyl-D-glucamine salts obtained are decomposed individually by addition of mineral acid, the (+)-form being isolated as a pure compound, then the (−)-form being racemized by known methods, and N-methyl-D-glucamine being recovered from the acidic mother liquors.

5. The process according to claims 1 or 2 wherein a solvent is used in which the solubility of the (−)-6-methoxy-α-methyl-2-naphthaleneacetic acid N-methyl-D-glucamine salt is at least 10 times the solubility of the (+)-6-methoxy-α-methyl-2-naphthaleneacetic acid N-methyl-D-glucamine salt at the resolution temperature.

6. A process for separating (+)-6-methoxy-α-methyl-2-naphthaleneacetic acid from a mixture of (+)- and (31)-6-methoxy-α-methyl-2-naphthaleneacetic acid or salts thereof comprising:

preparing a mixture of (+)- and (−)-6-methoxy-α-methyl-2-naphthaleneacetic acid or soluble salts thereof and N-methyl-D-glucamine or a salt thereof in an inert solvent to form the salts of (+)- and (−)-6-methoxy-α-methyl-2-naphthaleneacetic acid with N-methyl-D-glucamine, the salt of (+)-6-methoxy-α-methyl-2-naphthaleneacetic acid with N-methyl-D-glucamine being significantly less soluble in the inert solvent than is the salt of (−)-6-methoxy-α-methyl-2-naphthaleneacetic acid with N-methyl-D-glucamine at the temperature of crystallization, and crystallizing the salt of (+)-6-methoxy-α-methyl-2-naphthaleneacetic acid with N-methyl-D-glucamine from said mixture to yield a salt product enriched in the salt of (+)-6-methoxy-α-methyl-2-naphthaleneacetic acid with N-methyl-D-glucamine.

7. The process of claim 6 wherein said mixture is heated to solubilize the salts of (+)- and (−)-6-methoxy-α-methyl-2-naphthaleneacetic acid with N-methyl-D-glucamine in said inert solvent, and said salt of (+)-6-methoxy-α-methyl-2-naphthaleneacetic acid with N-methyl-D-glucamine is crystallized by cooling said heated mixture so as to subject said mixture to fractional crystallization to thereby obtain said salt product enriched in the salt of (+)-6-methoxy-α-methyl-2-naphthaleneacetic acid with N-methyl-D-glucamine.

8. The process of claims 6 or 7 further including the steps of dissolving said salt product enriched in the salt of (+)-6-methoxy-α-methyl-2-naphthaleneacetic acid with N-methyl-D-glucamine in an inert solvent therefor, cleaving said salt to yield (+)-6-methoxy-α-methyl-2-naphthaleneacetic acid, and crystallizing substantially pure (+)-6-methoxy-α-methyl-2-naphthaleneacetic acid therefrom.

9. The process of claim 6 wherein said mixture includes about 50 to about 100 molar percent of said N-methyl-D-glucamine based upon the (+)- and (−)-6-methoxy-α-methyl-2-naphthaleneacetic acid in said mixture.

10. The process of claim 6 wherein said mixture includes about 50–60 molar percent of said N-methyl-D-glucamine and about 50–40 molar percent of an inorganic base or an organic base, said molar percentages being based upon the (+)- and (−)-6-methoxy-α-methyl-2-naphthaleneacetic acid in said mixture.

11. The process of claim 10 wherein said inorganic base is sodium hydroxide or potassium hydroxide.

12. The process of claim 10 wherein said organic base is a trialkylamine.

13. The process of claim 10 wherein said organic base is triethylamine.

14. The process of claims 6 or 7 wherein the solvent comprises an alcohol.

15. The process of claims 6 or 7 wherein the solvent comprises methanol or isopropanol.

16. The process of claims 6 or 7 further including the step of treating the mother liquors to recover N-methyl-D-glucamine for recycling.

17. The process of claims 6 or 7 further including the steps of recovering a non-racemic mixture of (+)- and (−)-6-methoxy-α-methyl-2-naphthaleneacetic acid from the mother liquors, the mixture being enriched in (−)-6-methoxy-α-methyl-2-naphthaleneacetic acid, racemizing the mixture, and recycling said racemized mixture.

18. The process of claim 6 further including the steps of subjecting said crystalline salt product enriched in the salt of (+)-6-methoxy-α-methyl-2-naphthaleneacetic acid with N-methyl-D-glucamine to at least one additional recrystallization to obtain a product further enriched in the salt of (+)-6-methoxy-α-methyl-2-naphthaleneacetic acid with N-methyl-D-glucamine, and then dissolving said product further enriched in the salt of (+)-6-methoxy-α-methyl-2-naphthaleneacetic acid with N-methyl-D-glucamine in an inert solvent therefor, cleaving said product to yield (+)-6-methoxy-α-methyl-2-naphthaleneacetic acid, and crystallizing substantially pure (+)-6-methoxy-α-methyl-2-naphthaleneacetic acid therefrom.

19. The process of claim 8 further including the step of subjecting said substantially pure (+)-6-methoxy-α-methyl-2-naphthaleneacetic acid to at least one additional recrystallization to further increase the purity thereof.

* * * * *